United States Patent [19]

Lim et al.

[11] Patent Number: 5,698,703
[45] Date of Patent: Dec. 16, 1997

[54] SYN-ISOMER OF THIAZOLYL INTERMEDIATE AND PROCESS FOR THE PREPARATION THEREOF

[75] Inventors: Gary M. F. Lim, Fayetteville; John M. Roubie, East Syracuse, both of N.Y.

[73] Assignee: Bristol-Myers Squibb Company, Princeton, N.J.

[21] Appl. No.: 232,898

[22] Filed: Apr. 25, 1994

Related U.S. Application Data

[63] Continuation of Ser. No. 72,349, Jun. 4, 1993, abandoned, which is a continuation of Ser. No. 941,598, Sep. 8, 1992, abandoned, which is a continuation-in-part of Ser. No. 757,109, Sep. 10, 1991, abandoned.

[51] Int. Cl.$^6$ ................................................. C07D 277/40
[52] U.S. Cl. ............................................. 548/194; 540/222
[58] Field of Search .................................. 548/197, 194; 540/222

[56] References Cited

U.S. PATENT DOCUMENTS

| | | | |
|---|---|---|---|
| 4,203,899 | 5/1980 | Ochiai et al. | 540/222 |
| 4,385,181 | 5/1983 | Farge et al. | 540/222 |
| 4,406,899 | 9/1983 | Aburaki et al. | 540/222 |
| 4,754,031 | 6/1988 | Angerbauer et al. | 540/222 |
| 4,868,294 | 9/1989 | Brundidge et al. | 540/222 |
| 4,910,301 | 3/1990 | Kaplan et al. | 540/222 |
| 4,943,631 | 7/1990 | Looker | 540/222 |

FOREIGN PATENT DOCUMENTS

| | | |
|---|---|---|
| 238950 | 3/1987 | Czechoslovakia . |
| 160546 | 11/1985 | European Pat. Off. . |
| 2144424 | 3/1985 | United Kingdom . |

OTHER PUBLICATIONS

Chemical Abstracts vol. 110, 389,79d p. 544 (1989).
English Translation of Czechoslovak patent CS 238,950 (1987).
Mandel, et al., *Collect. Czech. Chem. Commun.*, 54: 1734–1745 (1989).

*Primary Examiner*—Robert Gerstl
*Attorney, Agent, or Firm*—Aldo A. Algieri

[57] ABSTRACT

The present invention provides a stable, crystalline syn-isomer of 2-(2-aminothiazol-4-yl)-2-methoxyimino acetyl chloride hydrochloride substantially free of the anti-isomer and a process for the preparation thereof which may be used in an acylation process for the preparation of useful broad-spectrum antibiotics.

8 Claims, 4 Drawing Sheets

SYN-ISOMER OF THIAZOLYL INTERMEDIATE AND PROCESS FOR THE PREPARATION THEREOF

CROSS-REFERENCE TO RELATED APPLICATION

This is a continuation of U.S. Ser. No. 08/072,349 filed Jun. 4, 1993, now abandoned which is a continuation of U.S. Ser. No. 07/941,598 filed Sep. 8, 1992, now abandoned which is a CIP of Ser. No. 07/757,109 filed Sep. 10, 1991, now abandoned.

BACKGROUND OF THE INVENTION

1. Field of the Invention

The present invention provides a stable, crystalline salt of the syn-isomer of a thiazolyl intermediate and a process for the preparation thereof which may be used in the preparation of useful broad spectrum antibacterial agents.

2. Background Art

A large number of cephalosporin antibiotics are known which contain a 2-(2-aminothiazol-4-yl)-(Z)-2-methoxyimino acetic acid side chain which is coupled to the 7-amino group of a cephalosporanic acid by well-known acylation procedures. In most instances, it is necessary to protect the amino moiety and activate the carboxylic acid of the side chain as part of the acylation procedure. Consequently, the art discloses a large number of amino-protecting groups for the 2-amino group of the thiazole ring and a large number of activating groups for the carboxylic acid. The search for newer protecting groups and activating groups to produce the desired antibiotic is still the subject of numerous publications in view of the costs and toxicities associated with certain activating groups. Therefore, there is still a need in the preparation of useful broad spectrum antibiotics for a simple, stable, crystalline, economical, and non-toxic side chain having the desired geometric (Z)-isomer which can be readily coupled to the 7-amino group of the cephalosporin nucleus. The following is representative of some of the art.

In U.S. Pat. No. 4,203,899 to Ochiai, et al., issued May 20, 1980, there is disclosed compounds of the formula

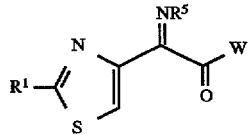

wherein $R^1$ represents amino, protected amino, hydroxyl, or protected hydroxyl; $R^5$ represents hydroxyl or protected hydroxyl; and W represents hydroxyl, $C_{1-4}$ alkoxy, halogen, or OM wherein M is an alkali metal.

U.K. Patent Application GB-2,144,424, published Mar. 6, 1985, discloses the preparation of a series of pyridinium cephalosporin derivatives by various methods, including the use of the compound of formula

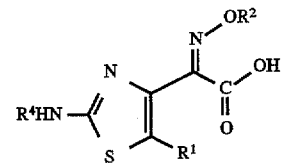

or a salt thereof wherein $R^1$ denotes a hydrogen or halogen atom; $R^2$ denotes a hydrogen atom or a $C_{1-6}$ alkyl radical, and $R^4$ represents hydrogen or an amino protective group, or with an activated derivative of this compound.

European Patent Application EP-160,546, published Nov. 6, 1985, also discloses the preparation of a series of cephalosporin compounds by various methods, including the use of the substituted oxyiminothiazolyl acetic acid compounds of formula

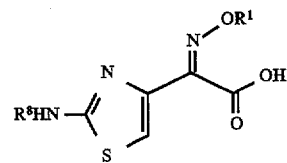

or a reactive derivative thereof, wherein $R^8$ represents a hydrogen atom or a protective group for an amino group. Suitable examples of such reactive derivatives which are disclosed are mixed acid anhydrides, acid anhydrides, acid halides, active esters, active amides, and acid azides.

In U.S. Pat. No. 4,385,181 to Farge, et al., issued May 24, 1983, there is disclosed thioloesters of the formula

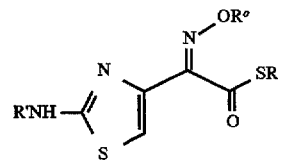

wherein R' represents hydrogen or a protecting radical, $R^o$ represents hydrogen, alkyl, vinyl, cyanomethyl, or a protecting radical, and R represents alkyl, L-2-amino-2-carboxyethyl, phenyl, or a large number of various heterocyclic radicals listed in columns 4 to 8, as well as their syn- and anti-isomers and mixtures thereof.

In addition to the above-cited references, there exists a large number of references which disclose various protecting groups for the 2-amino substituent and an even larger number of activating groups/leaving groups of the carboxylic acid moiety which may be used in the acylation of a 7-amino cephalosporin compound.

However, the most relevant art is Czechoslovak Patent No. 238,950, published Mar. 16, 1987, [Chemical Abstracts, Vol. 110, p. 544 (1989)] which discloses the compound of the instant invention having the formula

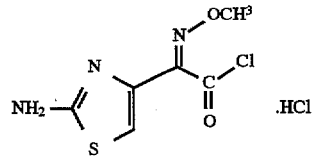

wherein the compound is alleged to have the syn configuration. The only evidence presented for the product in the patent is a chlorine content of 99% to 100.5% of the theoretical value.

In connection with work on the development of new synthetic methods for the production of antibiotics, the present inventors, as well as others in the art, have felt the need for simple, convenient, economical, crystalline, stable, and non-toxic starting materials for use in the manufacture of antibiotics. Initial attempts to prepare and use the acid chloride of 2-(2-aminothiazol-4-yl)-2-methoxyimino acetic acid without the use of protecting groups were unsuccessful. However, the present inventors have now found that the compound of the instant invention can be prepared under specifically defined reaction conditions. This finding was further confirmed by the present inventors when they could not reproduce the teachings of the above-cited Czechoslovak patent. The desired syn-isomer of the acid chloride hydrochloride, which is necessary to produce the desired antibiotic, could not be repeated. Furthermore, additional experiments confirmed that the teachings of the art did not produce the hydrochloride salt of the desired syn-isomer of the acid chloride substantially free of the anti-isomer and having a proton nuclear magnetic resonance spectrum ($^1$H NMR) as described herein.

The broad spectrum antibiotic cefepime is disclosed by Aburaki, et al, in U.S. Pat. No. 4,406,899, issued Sep. 27, 1983 and its preparation is described by two Reaction Schemes in which the reactants and products required the use of blocking and deblocking groups. In the reaction scheme actually exemplified, the product required a chromatographic purification step to separate the mixture of $\Delta^2$ and $\Delta^3$ isomers and the cefepime product thereby produced is in the zwitterion form. However, the zwitterion form of cefepime is unstable at room and elevated temperatures.

Murray A. Kaplan et al, in U.S. Pat. No. 4,910,301, issued Mar. 20, 1990, discloses temperature stable crystalline salts of cefepime in dry powder form having excellent room and superior elevated temperature stability compared to the zwitterion form of cefepime described by Aburaki et al, U.S. Pat. No. 4,406,899.

In U.S. Pat. No. 4,868,294, issued Sep. 19, 1989, Brundidge et al, describe the preparation of 7-amino-3-[(1-methyl-1-pyrrolidinio)methyl]ceph-3-em-4-carboxylate salts substantially free of the $\Delta^2$ isomer and their use in an aqueous acylation procedure to prepare the antibiotic cefepime as the sulfate salt.

In U.S. Pat. No. 4,754,031, issued Jun. 28, 1988, Angerbauer et al, describe a process for the preparation of several cephalosporin antibiotics including cefepime in the zwitterion form. Although this process does not use protecting groups, it does use an anhydride for activation in an aqueous acylation reaction which requires chromatographic purification steps to give the zwitterion form of cefepime.

In U.S. Pat. No. 4,943,631, issued Jul. 24, 1990, Brian E. Looker describes an improved process for the preparation of the antibiotic cefepime as a hydroiodide salt. The process controls the formation of the undesirable $\Delta^2$ isomer by employing a cephalosporin sulfoxide intermediate. However, the process described in the patent remains costly and inefficient since it introduces two additional steps to the prior art process and continues to use protecting groups which require blocking and deblocking procedures. Furthermore, the process requires the use of column chromatography as a purification method which is impractical on a manufacturing scale.

SUMMARY OF THE INVENTION

The present invention provides a stable, crystalline syn-isomer of 2-(2-aminothiazol-4-yl)-2-methoxyimino acetyl chloride hydrochloride substantially free of the anti-isomer and a process for the preparation thereof. The process is carried out by preparing the hydrochloride salt of the free acid followed by treatment with specific amounts of oxalyl chloride and dimethylformamide at reduced temperatures. The present invention also provides a process for the preparation of a cephalosporin antibiotic using the syn-isomer of 2-(2-aminothiazol-4-yl)-2-methoxyimino acetyl chloride hydrochloride substantially free of the anti-isomer.

DETAILED DESCRIPTION OF THE INVENTION

Figure 1:
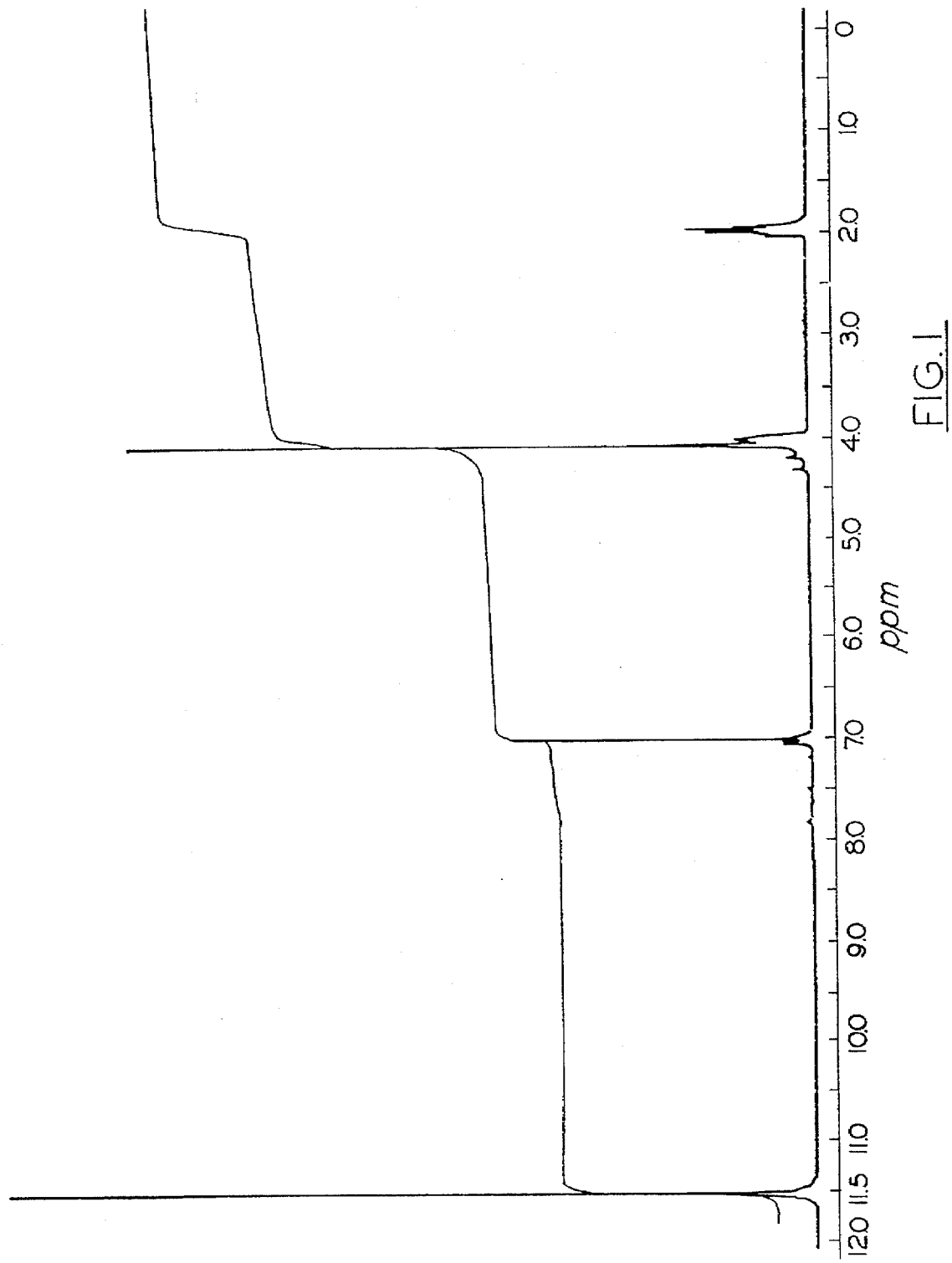
FIG. 1 shows the proton nuclear magnetic resonance spectrum of syn 2-(2-aminothiazol-4-yl)-2-methoxyimino acetyl chloride hydrochloride of Example 10 in acetic acid-$d_4$ (100 MHz).

This invention provides a stable, crystalline syn-isomer of 2-(2-aminothiazol-4-yl)-2-methoxyimino acetyl chloride hydrochloride which is substantially free of the anti-isomer and is represented by Formula III.

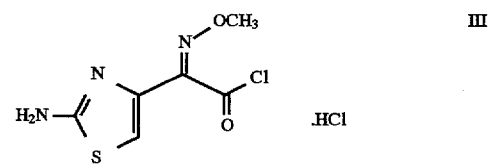

As a result of being substantially free of the anti-isomer, Compound III is convertible to broad spectrum cephalosporins which themselves are substantially free of the anti-isomer, without the need for chromatographic separation of the syn- and anti-isomers. As a result of the enhanced stability, Compound III may be isolated and stored and, when desired, Compound III may be converted to end products in a different solvent which is advantageous for the production of the desired antibiotic substantially free of the $\Delta^2$ isomer. An additional advantage of the intermediate of Formula III is that it does not require blocking (protection) of the amino group prior to acylation or deblocking (deprotection) of the amino group after acylation, thus, offering process efficiency. A further advantage of the acid chloride of Formula III is its use in an acylation process to produce broad-spectrum cephalosporins and, in particular, cefepime. In contrast to other methods such as described in Aburaki, et al., U.S. Pat. No. 4,406,899, the intermediate of Formula III has a chloride ion as a simple and non-toxic leaving group with no precaution necessary to remove it from the desired antibiotic as is the instance with most other leaving groups known in the art. Also, some of the intermediates known in the art which contain other leaving groups are difficult to prepare while other intermediates which contain leaving groups such as 2-mercaptobenzothiazole have been found to be toxic [*Chem. Abstracts.*, 1989, Vol. 111 (3), 19243p].

As defined herein and in the claims, the term "substantially free" means that the compound contains less than about 5% of the undesirable isomer. Preferably, the compound contains less than about 2% of the undesirable isomer.

vent and temperature, are critical in the process for the preparation of the syn-isomer of Compound III which is substantially free of the anti-isomer.

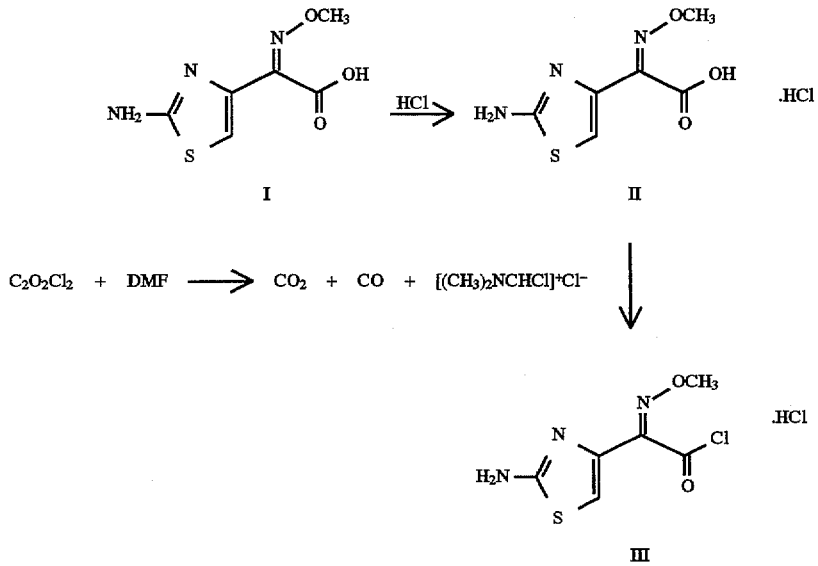

Reaction Scheme 1

The syn-isomer of the acid chloride hydrochloride of Formula III may be prepared from the syn-isomer of the acid of Formula I as outlined in Reaction Scheme 1. The acid of Formula I is first converted to the corresponding hydrochloride salt of Formula II by methods known in the art and then, if desired, isolated as an anhydrous, crystalline compound of Formula II. The formation of the hydrochloride salt is advantageously carried out with at least one molar equivalent of gaseous hydrogen chloride in an inert organic solvent such as toluene, acetonitrile, dichloromethane, acetone, benzene, xylene, cyclohexane, hexanes, dioxane or diethyl ether at a temperature of about −10° C. to about 50° C. Preferably, the reaction is carried out in toluene, dichloromethane or acetonitrile and acid hydrochloride of Formula II may be isolated or used in situ. When the reaction is conducted in acetonitrile, the resulting hydrochloride of Formula II tends to retain loosely bound solvent. Consequently, it is advantageous to use the acid hydrochloride of Formula II from acetonitrile in a reasonable period of time in the next step to avoid solvate displacement by atmospheric moisture. Most preferably, the reaction is carried out in toluene or dichloromethane at about 0° C. to room temperature.

The acid salt of Formula II is then advantageously treated with a chlorinating agent and, most preferably, with oxalyl chloride in combination with dimethylformamide to produce the stable, crystalline syn-isomer of Compound III. As demonstrated herein, the use of other known chlorinating agents can result in isomerization to give the undesirable anti-isomer or mixtures of syn- and anti-isomers. Additionally, chlorinating agents, such as phosphorous pentachloride, may result in the chlorination of the 5-position on the thiazole ring which would then result in an undesirable impurity in the antibiotic. The present inventors have discovered that, in addition to the preparation of the acid hydrochloride of Formula II, the appropriate selection of chlorinating agent and reaction conditions, such as sol- Chlorinating methods, which are generally used for activating acids, are well-known in the art. Phosphorous pentachloride, which is the most widely used chlorinating agent, is not suitable for the chlorination of Compound II since it also results in the isomerization of the methoxyimino group to produce the undesirable anti-isomer of Compound III. This is clearly demonstrated in Examples 12, 13, 14, and 16 as described herein. Another known chlorinating method is the use of oxalyl chloride in combination with dimethylformamide. However, the present inventors have discovered that the oxalyl chloride method, wherein dimethylformamide is used as a catalyst, does not produce substantial amounts of the desired syn-isomer of Compound III. This is also clearly demonstrated in Example 15 as described herein. After extensive studies, the present inventors have discovered that the use of dimethylformamide in an amount less than an equimolar amount relative to the amount of oxalyl chloride is deleterious to the production of the desired syn-isomer of the acid chloride hydrochloride of Formula III. Most preferably, the molar amount of dimethylformamide should exceed the molar amount of oxalyl chloride. The inventors have also found that the use of excess molar amounts of dimethylformamide is also deleterious to both the reaction and to the stability of the desired product. Thus, the inventors have discovered a method to control the instability of the reaction materials to either excess chloride ion generated by oxalyl chloride or excess dimethylformamide which are critical for production of the stable, crystalline syn-isomer of Compound III which is substantially free of the anti-isomer. In the instance, when the conversion of the compound of Formula II to the compound of Formula III is not complete, there will remain a small amount of the syn-isomer of the acid of Formula II in the isolated product of Compound III. The presence of some unreacted Compound II in the product of Compound III and small amounts of the anti-isomer of Compound III do not affect the subsequent acylation reaction for the successful production of the desired antibiotic which is substantially free of the anti-isomer of said antibiotic.

The present inventors have also found that the temperature and reaction solvent of the chlorinating reaction are also critical. Preferably, the reaction is conducted in an inert organic solvent, such as dichloromethane, chloroform or acetonitrile, at a temperature of less than −10° C. Most preferably, the reaction is advantageously carried out in dichloromethane at about −15° C. to about −40° C.

ammonium hydroxide, primary amine, secondary amine, tertiary amine or the like to neutralize the hydrochloric acid which is thereby produced. Preferably, the organic bases which may be used in the process are, for example, diethylamine, triethylamine, diisopropylethylamine, N-methylmorpholine, 2,6-lutidine, N,N-dimethylaniline, N,N-diethylaniline or the like. Most preferably, the base is ammonium hydroxide, triethylamine or N-methylmorpholine.

Reaction Scheme 2

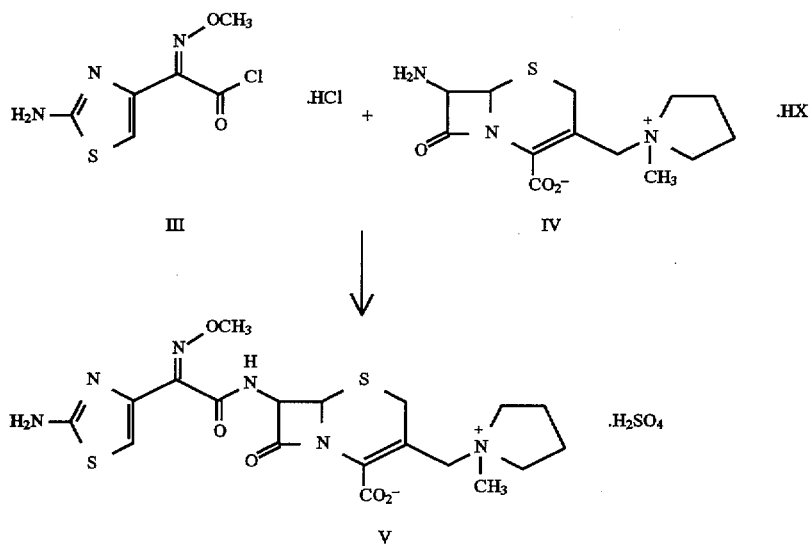

The use of the syn-isomer of the acid chloride hydrochloride of Formula III to prepare useful broad-spectrum antibiotics by way of a general acylation reaction is illustrated in Reaction Scheme 2. More specifically, Reaction Scheme 2 illustrates the use of the acid chloride of Formula III to prepare the broad spectrum antibiotic cefepime which is substantially free of the anti-isomer and the $\Delta^2$ isomer. Furthermore, the acid chloride hydrochloride of Formula III may be used to prepare cephalosporin antibiotics having the syn-isomer of 2-(2-aminothiazol-4-yl)-2-methoxyimino acetyl attached to the 7-amino group of the cephalosporin nucleus such as cefodizime, cefmenoxime, cefotaxime, cefpirome, cefpodoxime, cefquinome, cefteram, ceftiofur, cefetamet and cefuzonam.

In another aspect, there is provided an acylation process for the preparation of the broad-spectrum antibiotic cefepime which is substantially free of the anti-isomer and the $\Delta^2$-isomer. The 7-amino-3-[(1-methyl-1-pyrrolidinio)-methyl]ceph-3-em-4-carboxylate salt which is substantially free of the $\Delta^2$ isomer and represented by Formula IV wherein HX is HCl, HI or $H_2SO_4$ may be treated with the syn-isomer of 2-(2-aminothiazol-4-yl)-2-methoxyimino acetyl chloride hydrochloride which is substantially free of the anti-isomer and represented by Formula III in an aqueous or, preferably, mixed aqueous-organic solvent under carefully controlled pH conditions.

Suitable solvents which may be used in the process are aqueous-organic solvents such as water with ethanol, isopropanol, acetone, tetrahydrofuran, acetonitrile, dioxane, dimethylacetamide, dimethylformamide or the like. The pH of the process is controlled by titrating with a suitable inorganic or organic base such as sodium hydroxide, sodium carbonate, sodium bicarbonate, potassium hydroxide, The acylation is advantageously carried out at a pH of about 5 to about 7.5 and, preferably, at a pH of about 6.2 to 6.8. The process may be carried out at a temperature of about −10° C. to about 50° C. and, preferably, at about room temperature. After the acylation is completed, the reaction mixture is acidified with an appropriate acid and, preferably, with sulfuric acid to a pH of about 1.8 to 2.6 to produce the sulfate salt of the desired cefepime antibiotic which is substantially free of the anti-isomer and the $\Delta^2$ isomer. If desired, the sulfate salt of cefepime may be converted to other cefepime salts such as the dihydrochloride hydrate as described by Kaplan, et al, in U.S. Pat. No. 4,910,301. The utility of Compound V is shown in Abruaki, et al, U.S. Pat. No. 4,406,899.

Furthermore, to confirm that the acid chloride hydrochloride product of the prior art is in the anti-isomer and not in the desired syn-isomer, the present inventors substituted the product of the prior art such as that produced in Example 14 for the syn-isomer of the compound of Formula III in the acylation reaction illustrated in Reaction Scheme 2. The resulting cephalosporin product which was produced as described in Examples 17 and 18 was compared to the cefepime antibiotic produced by the present invention. As can be seen by the comparison in Example 19, the anti-cefepime produced by teachings of the prior art is not the same as the useful broad-spectrum syn-cefepime produced by use of the present invention.

In one aspect of the present invention, there is provided a stable, crystalline syn-isomer of 2-(2-aminothiazol-4-yl)-2-methoxyimino acetyl chloride hydrochloride substantially free of the anti-isomer having the formula

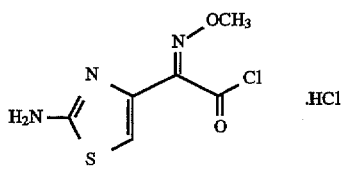

In another aspect of the present invention, there is provided a process for the preparation of a stable, crystalline syn-isomer of 2-(2-aminothiazol-4-yl)-2-methoxyimino acetyl chloride hydrochloride substantially free of the anti-isomer which comprises reacting the anhydrous crystalline acid hydrochloride salt of the syn-isomer of 2-(2-aminothiazol-4-yl)-2-methoxyimino acetic acid with a mixture containing at least one molar equivalent of oxalyl chloride and at least one molar equivalent to a slight excess of dimethylformamide to an amount of said oxalyl chloride in an inert organic solvent at a temperature of less than −10° C. to produce a stable, crystalline syn-isomer of 2-(2-aminothiazol-4-yl)-2-methoxyimino acetyl chloride hydrochloride substantially free of the anti-isomer.

In still another aspect, there is provided a process for the preparation of an antibiotic, cefepime salt which is substantially free of the anti-isomer and the $\Delta^2$ isomer which comprises reacting 7-amino-3-[(1-methyl-1-pyrrolidinio)methyl]-ceph-3-em-4-carboxylate with the syn-isomer of 2-(2-aminothiazol-4-yl)-2-methoxyimino acetyl chloride hydrochloride substantially free of the anti-isomer in an aqueous-organic solvent at a pH of about 5.0 to 7.5.

DESCRIPTION OF SPECIFIC EMBODIMENTS

Example 1

Syn 2-(2-Aminothiazol-4-yl)-2-methoxyimino Acetic Acid Hydrochloride Salt

A suspension of (25 g, 124.25 mmol) 2-(2-aminothiazol-4-yl)-2-methoxyimino acetic acid in toluene (250 ml) was gassed with HCl at 20°–28° C. The HCl was introduced subsurface in two aliquots of 8.1 g (222.2 mmol) and 4.8 g (131.7 mmol) with 30 minutes agitation between aliquots. After 1 hour at 20° C., the product was collected by filtration under a nitrogen atmosphere, washed with toluene (50 ml) and hexane (250 ml), and dried at 20°–25° C. in vacuo to yield 28.68 g (97%) of the title compound.

Example 2

Syn 2-(2-Aminothiazol-4-yl)-2-methoxyimino Acetyl Chloride Hydrochloride

To a solution of (0.77 ml, 10 mmol) dimethylformamide in dichloromethane (40 ml) at 5° C. was added (0.89 ml, 10 mmol) 98% oxalyl chloride in dichloromethane (4.1 ml). Dropwise addition kept the temperature at 4°–5° C. To the resulting suspension, cooled to −27° C., was added (2.37 g, 10 mmol) 2-(2-aminothiazol-4-yl)-2-methoxyimino acetic acid hydrochloride prepared in Example 1. The suspension was stirred for 2.5 hours at −25° C. Filtration under a nitrogen atmosphere and washing with dichloromethane (50 ml) and hexane (100 ml) gave 1.78 g (69.5%) of white, crystalline title compound after drying at 20° C. in vacuo.

The title acid chloride acylated 7-amino desacetoxy cephalosporanic acid diphenylmethyl ester hydrochloride in pyridine solution to give a single zone (TLC) product coincident with and inseparable from an authentic sample of the desired desacetoxy cephalosporin ester.

Example 3

Syn 2-(2-Aminothiazol-4-yl)-2-methoxyimino Acetyl Chloride Hydrochloride

To a solution of (1.55 ml, 20 mmol) dimethylformamide in dichloromethane (80 ml) at 5° C. was added (1.78 ml, 20 mmol) of 98% pure oxalyl chloride in dichloromethane (8.2 ml). Addition time was 5 minutes at 5°–8° C. The resulting suspension was agitated 10 minutes at 5° C. and then cooled to −30° C. 2-(2-Aminothiazol-4-yl)-2-methoxyimino acetic acid hydrochloride (4.75 g, 20 mmol) from Example 1 was added. The suspension was stirred for 2.5 hours at −25° to −30° C. Filtration under a nitrogen atmosphere and washing with dichloromethane (75 ml) and hexane (100 ml) gave 3.57 g (69.7%) of crystalline title compound after drying at 20° C. in vacuo.

An aliquot of the solid acid chloride hydrochloride product acylated 7-amino desacetoxy cephalosporanic acid diphenylmethyl ester hydrochloride in pyridine solution to give essentially single zone (TLC) product which was coincident with and inseparable from an authentic sample of the desired desacetoxy cephalosporin ester.

Example 4

Preparation of 7-[2-(2-Aminothiazol-4-yl)-2-(Z)-methoxyiminoacetamido]-3-[(1-methyl-1-pyrrolidinio)methyl]ceph-3-em-4-carboxylate (Cefepime)

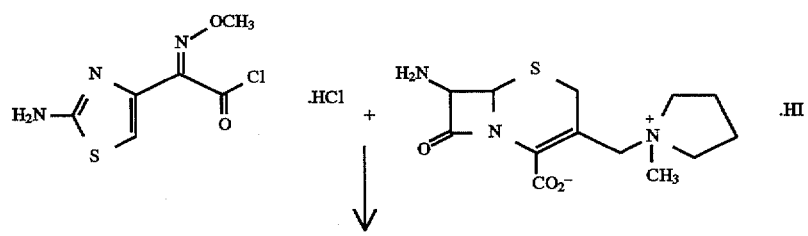

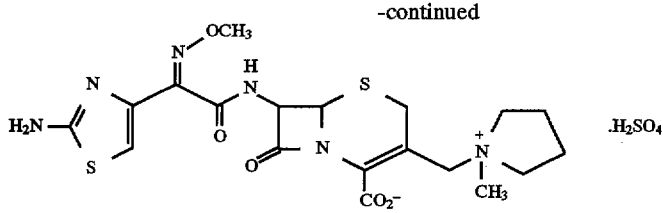

.H₂SO₄

7-Amino-3-[(1-methyl-1-pyrrolidinio)methyl]ceph-3-em-4-carboxylate monohydriodide (0.85 g, 2.0 mmol) [prepared according to the procedures described by S. P. Brundidge, et al., in U.S. Pat. No. 4,714,760] was dissolved in 9 ml of acetone-water (2:1) with triethylamine at pH 6.5 and 20° C. Syn 2-(2-aminothiazol-4-yl)-2-methoxyimino acetyl chloride hydrochloride (0.56 g, 2.2 mmol) [prepared in Example 3] was added using triethylamine to control the pH in the 5–7 range. Assay of the resulting solution by high pressure liquid chromatography showed 58% yield of the desired cephalosporin (cefepime). Acidification with sulfuric acid to pH 2.2 gave 0.63 g of the title antibiotic as its sulfate salt (51% activity yield), as described by Aburaki, et al., in U.S. Pat. No. 4,406,899, issued Sep. 27, 1983, and by Kaplan, et al, in U.S. Pat. No. 4,910,301, issued Mar. 20, 1990.

Example 5

Syn 2-(2-Aminothiazol-4-yl)-2-methoxyimino Acetyl Chloride Hydrochloride

To a solution of (9.75 ml, 125.9 mmol) dimethylformamide in dichloromethane (450 ml) at 5° C. was added dropwise a solution of (11.21 ml, 125.9 mmol) oxalyl chloride (98%) in dichloromethane (15 ml). Addition was completed in 10 minutes at 5°–7° C. To the resulting slurry, cooled to −25° C., was added (28.5 g, 119.9 mmol) syn 2-(2-aminothiazol-4-yl)-2-methoxyimino acetic acid hydrochloride salt in one aliquot. The slurry was stirred for 3.5 hours at −25° to −30° C., filtered under a nitrogen atmosphere, washed with dichloromethane (100 ml) and hexane (400 ml), and dried at 20°–25° C. in vacuo. Yield of crystalline title compound was 30.7 g (72.5%).

The title acid chloride acylated 7-amino desacetoxy cephalosporanic acid diphenylmethyl ester hydrochloride in pyridine solution to give essentially one zone (TLC) of the desired desacetoxy cephalosporin ester by reference to an authentic sample.

The title acid chloride (200 mg, 0.8 mmol) was hydrolyzed in water. $^1$H NMR of the isolated product was identical to the starting syn acid.

Example 6

Syn 2-(2-Aminothiazol-4-yl)-2-methoxyimino Acetyl Chloride Hydrochloride

To a solution of (8.13 ml, 105 mmol) dimethylformamide in dichloromethane (350 ml) at 5° C. was added dropwise (9.34 ml, 105 mmol) oxalyl chloride (98% pure) in dichloromethane (5 ml). Maximum temperature reached during the addition was 7° C. The resulting suspension was stirred for 10 minutes at 5° C. and then cooled to −27° C. 2-(2-Aminothiazol-4-yl)-2-methoxyimino acetic acid hydrochloride (23.8 g, 100 mmol) was added in one aliquot. The suspension was stirred for 2.5 hours at −25° to −30° C., filtered under a nitrogen atmosphere, washed with dichloromethane (25 ml) and hexane (125 ml), and dried at 20° C. in vacuo. Yield was 21.39 g (83.5%) of crystalline acid chloride hydrochloride.

Anal. Calcd. for $C_6H_7N_3O_2SCl_2$: C, 28.14; H, 2.76; N, 16.41; S, 12.52; Found: C, 28.25; H, 2.93; N, 16.32; S, 12.67.

$^1$H NMR (DMSO-$d_6$) δ: 3.93 ($CH_3$), 7.04 (H5).

Example 7

Syn 2-(2-Aminothiazol-4-yl)-2-methoxyimino Acetic Acid Hydrochloride Salt

A suspension of (87 g, 432.4 mmol) syn 2-(2-aminothiazol-4-yl)-2-methoxyimino acetic acid in toluene (870 ml) at 22° C. was gassed with two aliquots of HCl; 17.5 g, 480 mmol in 30 minutes and 15.0 g, 410 mmol in 20 minutes with 20 minutes agitation between aliquots. The slurry was agitated 1.5 hours at 25° C., filtered under a nitrogen atmosphere, washed with toluene (100 ml) and hexane (400 ml), and dried at 20°–25° C. in vacuo. Yield of the title compound was 100.2 g (97.5%).

Anal. Calcd. for $C_6H_8N_3O_3SCl$: C, 30.32; H, 3.39; N, 17.68; S, 13.49; Cl, 14.92; Found: C, 30.51; H, 3.39; N, 17.54; S, 13.37; Cl, 14.90.

Example 8

Syn 2-(2-Aminothiazol-4-yl)-2-methoxyimino Acetyl Chloride Hydrochloride

To a solution of (32.4 ml, 419.7 mmol) dimethylformamide in dichloromethane (400 ml) at 5° C. was added (37.4 ml, 419.7 mmol) 98% oxalyl chloride dropwise. The resulting suspension was cooled to −25° C. and added to a −25° C. suspension of (95 g, 399.7 mmol) syn 2-(2-aminothiazol-4-yl)-2-methoxyimino acetic acid hydrochloride from Example 7. The suspension was stirred for 2.5 hours at −25° to −28° C., filtered under a nitrogen atmosphere, washed with dichloromethane (100 ml) and hexane (500 ml), and dried at 20°–25° C. in vacuo. The yield of crystalline title compound was 84.3 g (82.3%).

Anal. Calcd. for $C_6H_7N_3O_2SCl_2$: C, 28.14; H, 2.76; N, 16.41; S, 12.52; Found: C, 27.90; H, 3.10; N, 16.14; S, 12.27.

$^1$H NMR (DMSO-$d_6$) δ: 3.95 ($CH_3$), 7.04 (H5).

Example 9

Preparation of 7-[2-(2-Aminothiazol-4-yl)-2-(Z)-methoxyiminoacetamido]-3-[(1-methyl-1-pyrrolidinio)methyl]ceph-3-em-4-carboxylate (Cefepime)

To a solution of 240 ml acetone and 80 ml water was added 20.0 g of 7-amino-3-[(1-methyl-1-pyrrolidinio) methyl]-ceph-3-em-4-carboxylate hydroiodide (0.047 mol) and set stirring. Using a Radiometer ABU80 auto titrator with end point set at pH 6.5 and filled with N-methylmorpholine, syn 2-(2-aminothiazol-4-yl)-2-methoxyimino acetyl chloride hydrochloride (20.0 g, 0.0785 mol) [prepared in Example 5] was added in 4 portions at 5 minute intervals keeping the pH at 6.5. After the addition was completed, the thin slurry was stirred for an additional 20 minutes at room temperature. The pH of the reaction mixture was lowered to pH 2.65 with 21 ml of 6N $H_2SO_4$. Precipitation of the title compound occurred. The slurry was seeded and stirred at room temperature for 20 minutes. The pH of the slurry was readjusted to 1.8 with 16 ml of 6N $H_2SO_4$, and stirring was continued for another 60 minutes. The slurry was filtered in vacuo and washed with 70 ml water-acetone (1:1) and then 70 ml acetone to give 24.09 g (88.5% stoich. weight yield) of the title compound, which is identical to the compound of Example 4 and to the cefepime described by Aburaki, et al., in U.S. Pat. No. 4,406,899, issued Sep. 27, 1983, and by Kaplan, et al, in U.S. Pat. No. 4,910,301, issued Mar. 20, 1990.

Example 10

Preparation of Syn 2-(2-Aminothiazol-4-yl)-2-methoxyimino Acetyl Chloride Hydrochloride To a solution of dimethylformamide (8.76 ml, 0.113 mole) in dichloromethane (375 ml) at 5° C., add oxalyl chloride (9.64 ml, 0.111 mole) dropwise keeping the temperature at 5°–6° C. Agitate the suspension for 10 minutes and then cool to –25° C. Add syn 2-(2-aminothiazol-4-yl)-2-methoxyimino acetic acid hydrochloride salt (25.0 g) in aliquots over 11 minutes under a dry nitrogen atmosphere. Agitate the slurry for 2.5 hours at –25° C. Filter the product in a dry nitrogen atmosphere, and wash the cake with dichloromethane (80 ml). Dry the product at 20°–25° C. in vacuo over $P_2O_5$ to yield 23.88 g (88.6%) of the title compound as a pale-yellow, crystalline solid.

Anal. Calcd. for $C_6H_7N_3O_2SCl_2$: C, 28.14; H, 2.76; N, 16.41; S, 12.52; Cl, 27.68; Found: C, 28.06; H, 2.71; N, 16.26; S, 12.30; Cl, 27.23.

The product of the foregoing experiment was characterized by proton nuclear magnetic resonance spectrum in acetic acid-$d_4$ ($^1$H NMR), as shown in FIG. 1.

$^1$H NMR ($CD_4CO_2D$) δ: 4.14 ($CH_3$), 7.10 (H5). Residual acid hydrochloride level from $CH_3$ (4.11) integral is 5.1%. A trace level of isomeric H5 is seen at 7.67 ppm.

Example 11

Syn 2-(2-Aminothiazol-4-yl)-2-methoxyimino Acetyl Chloride Hydrochloride

To a solution of dimethylformamide (17.92 ml, 231.9 mmol) in dichloromethane (375 ml) at 5° C. was added oxalyl chloride (19.76 ml, 220.8 mmol). Addition time was 15 minutes at 5°–6° C. The resulting suspension was agitated 10 minutes at 5°–6° C. and then cooled to –25° C. 2-(2-Aminothiazol-4-yl)-2-methoxyimino acetic acid hydrochloride (25.0 g, 105.2 mmol) was added. The resulting solution was seeded with the title compound to produce the product slurry. The suspension was agitated for 3.5 hours at –25° C., filtered in a dry nitrogen atmosphere, washed with dichloromethane (150 ml), and dried at 20°–25° C. in vacuo. Yield was 9.61 g (35.7%) of crystalline title compound.

An aliquot of the solid acid chloride hydrochloride product acylated 7-amino desacetoxy cephalosporanic acid diphenylmethyl ester hydrochloride in pyridine solution to give essentially single zone (TLC) product which was coincident with and inseparable from an authentic sample of the desired desacetoxy cephalosporin ester.

Example 12

Preparation of 2-(2-Aminothiazol-4-yl)-2-methoxyimino Acetyl Chloride Hydrochloride The experimental procedure of Example 1 in Czechoslovakian Patent No. 238,950 was repeated as follows:

A sample of syn 2-(2-aminothiazol-4-yl)-2-methoxyimino acetic acid (4.0 g) having a KF of 0.06% was slurried in 30 ml of benzene at 21° C. One drop of dimethylformamide was added, followed by 5.0 grams of powdered phosphorous pentachloride in one aliquot. The temperature rose to 34° C. in approximately 2 minutes and was then raised to 40° C. in 1 minute to provide a complete solution. The solution was allowed to cool, and at 36° C., a precipitate formed. After stirring for 30 minutes, the temperature was 22° C. The light-yellow solid was collected by filtration under a dry nitrogen atmosphere and washed with 30 ml of benzene and 20 ml of heptane. Yield was 2.88 g after drying in vacuo over $P_2O_5$ at 20°–25° C. for 18 hours.

Figure 2:
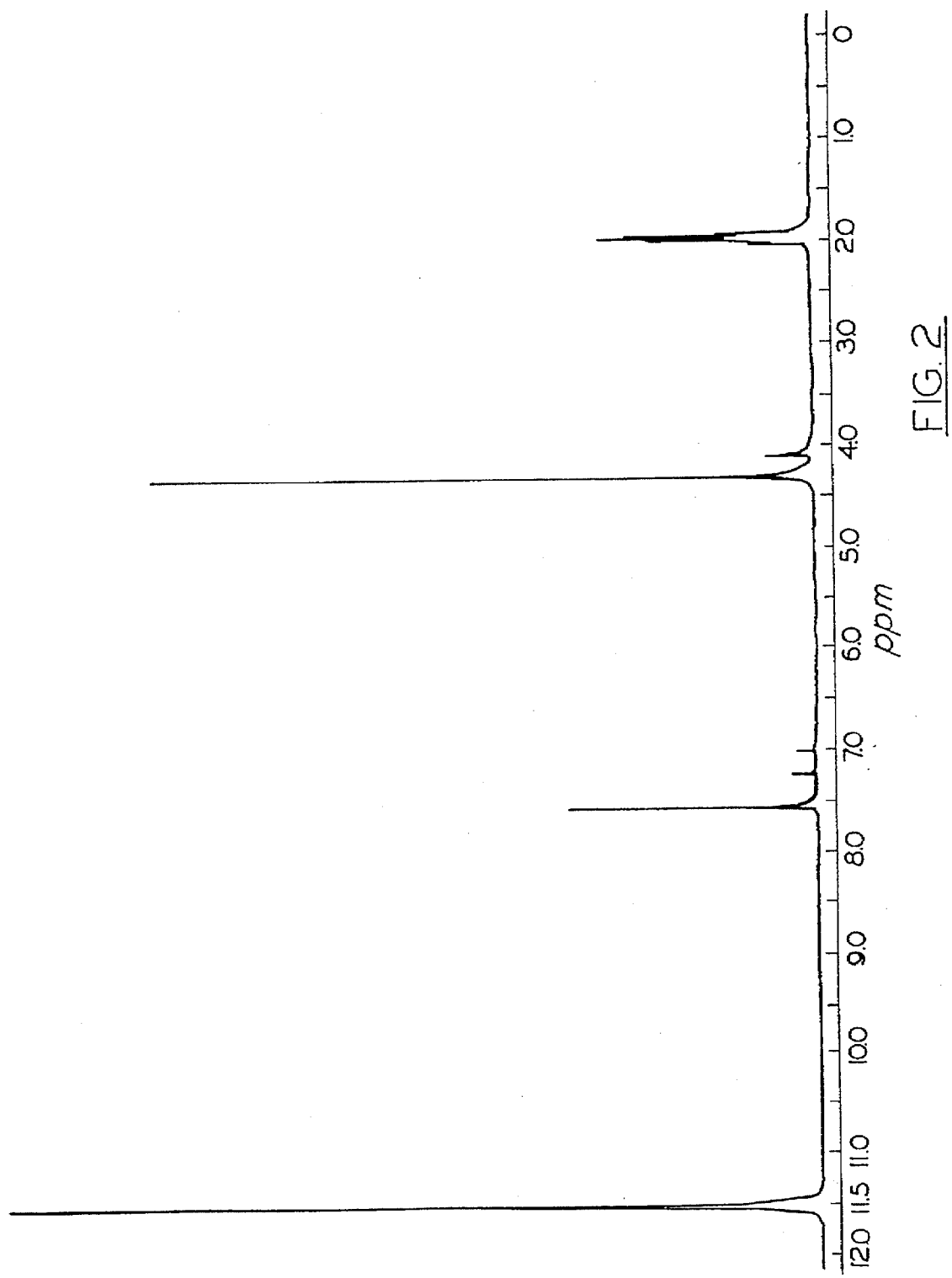
FIG. 2 shows the proton nuclear magnetic resonance spectrum of the product of Example 12 in acetic acid-$d_4$ (100 MHz).

The product of the foregoing experiment was characterized by proton nuclear magnetic resonance spectrum in acetic acid-$d_4$ ($^1$H NMR) as shown in FIG. 2 which shows the H5 at 7.56 ppm and $CH_3$ at 4.34 ppm. This spectrum is consistent with a product of the title compound having the anti-isomer configuration and not the syn-isomer as disclosed by said Czechoslovakian patent.

Example 13

Preparation of 2-(2-Aminothiazol-4-yl)-2-methoxyimino Acetyl Chloride Hydrochloride The experimental procedure of Example 2 in Czechoslovakian Patent No. 238,950 was repeated as follows:

A sample of syn 2-(2-aminothiazol-4-yl)-2-methoxyimino acetic acid (4.0 g) having a KF of 0.06% was slurried in 20 ml of acetonitrile which had been adjusted to have a KF of 0.22%. A drop of dimethylformamide was added, and the temperature was 20° C. On addition of 6.0 grams of powdered phosphorus pentachloride, the temperature rose to 40° C. and complete solution was obtained. The solution was cooled to 20° C., and a precipitate formed at 33° C. After stirring for 30 minutes, the product was collected under a dry nitrogen atmosphere and washed with 30 ml of benzene and 20 ml of heptane. Yield was 1.86 g after drying for 18 hours at 20°–25° C. in vacuo over $P_2O_5$.

Figure 3:
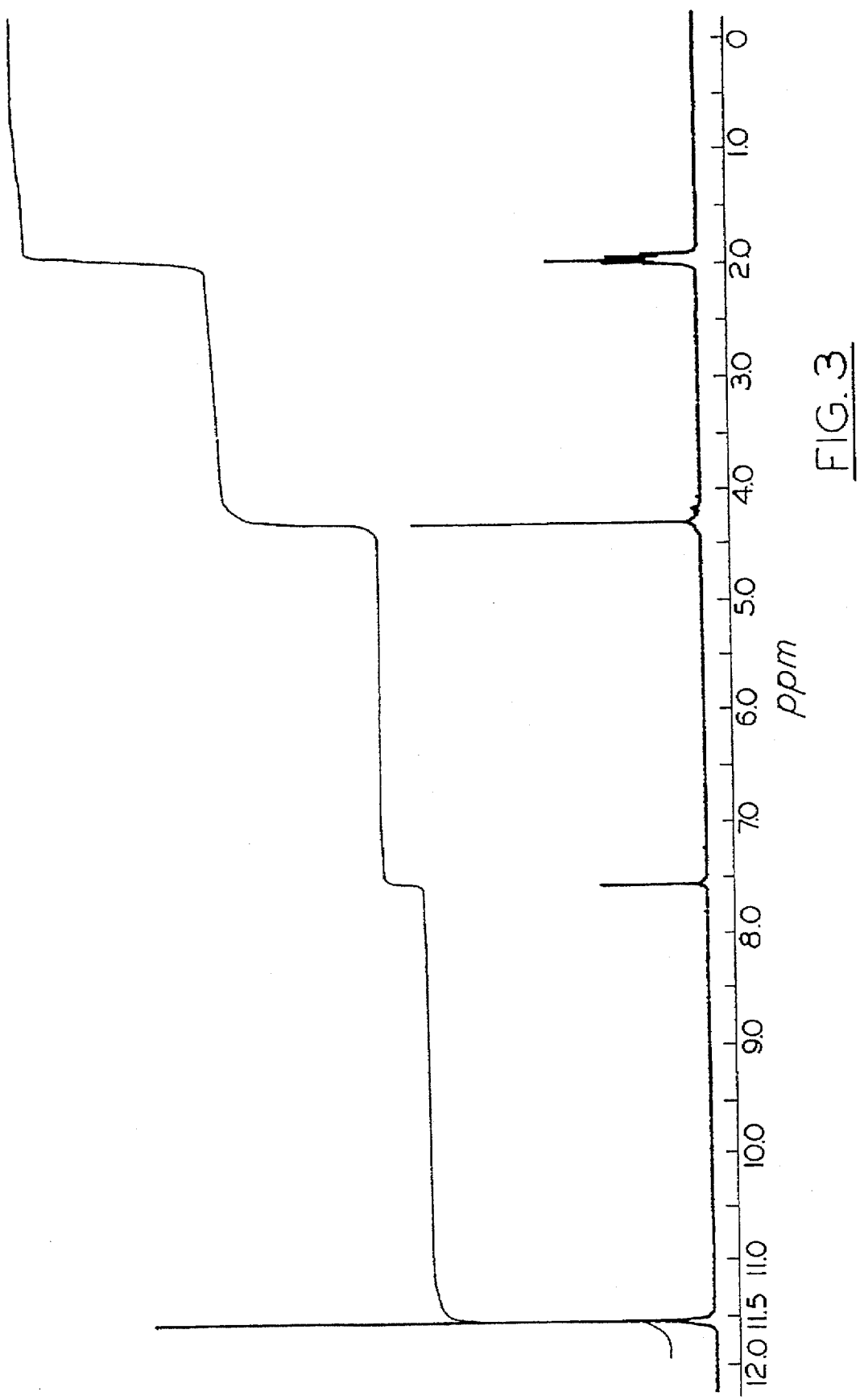
FIG. 3 shows the proton nuclear magnetic resonance spectrum of the product of Example 13 in acetic acid-$d_4$ (100 MHz).

The product of the foregoing experiment was characterized by proton nuclear magnetic resonance spectrum in acetic acid-$d_4$ ($^1$H NMR) as shown in FIG. 3 which shows the H5 at 7.56 ppm and $CH_3$ at 4.31 ppm. The $^1$H NMR spectrum is consistent with a product of the title compound having the anti-isomer configuration and not the syn-isomer as disclosed by said Czechoslovakian patent.

Example 14

Preparation of 2-(2-Aminothiazol-4-yl)-2-methoxyimino Acetyl Chloride Hydrochloride The experimental procedure of Example 3 in Czechoslovakian Patent No. 238,950 was repeated as follows:

Concentrated hydrochloric acid (0.16 ml) was added to 30 ml of dichloromethane. After cooling to −10° C., 6.5 g of phosphorus pentachloride was added in increments. After warming to 0° C., 4.0 g of syn 2-(2-aminothiazol-4-yl)-2-methoxyimino acetic acid having a KF of 0.06% was added in one aliquot. The temperature rose to 2° C. A complete solution was obtained after 9 minutes at 0° C. After 40 minutes, a precipitate started to form. The product slurry was agitated for 2.8 hours at 2°–3° C., filtered under a dry nitrogen atmosphere, washed with 30 ml of benzene and 20 ml of heptane, and dried in vacuo at 20°–25° C. over $P_2O_5$ for 18 hours. The yield was 3.42 g of light-yellow powder.

Figure 4:
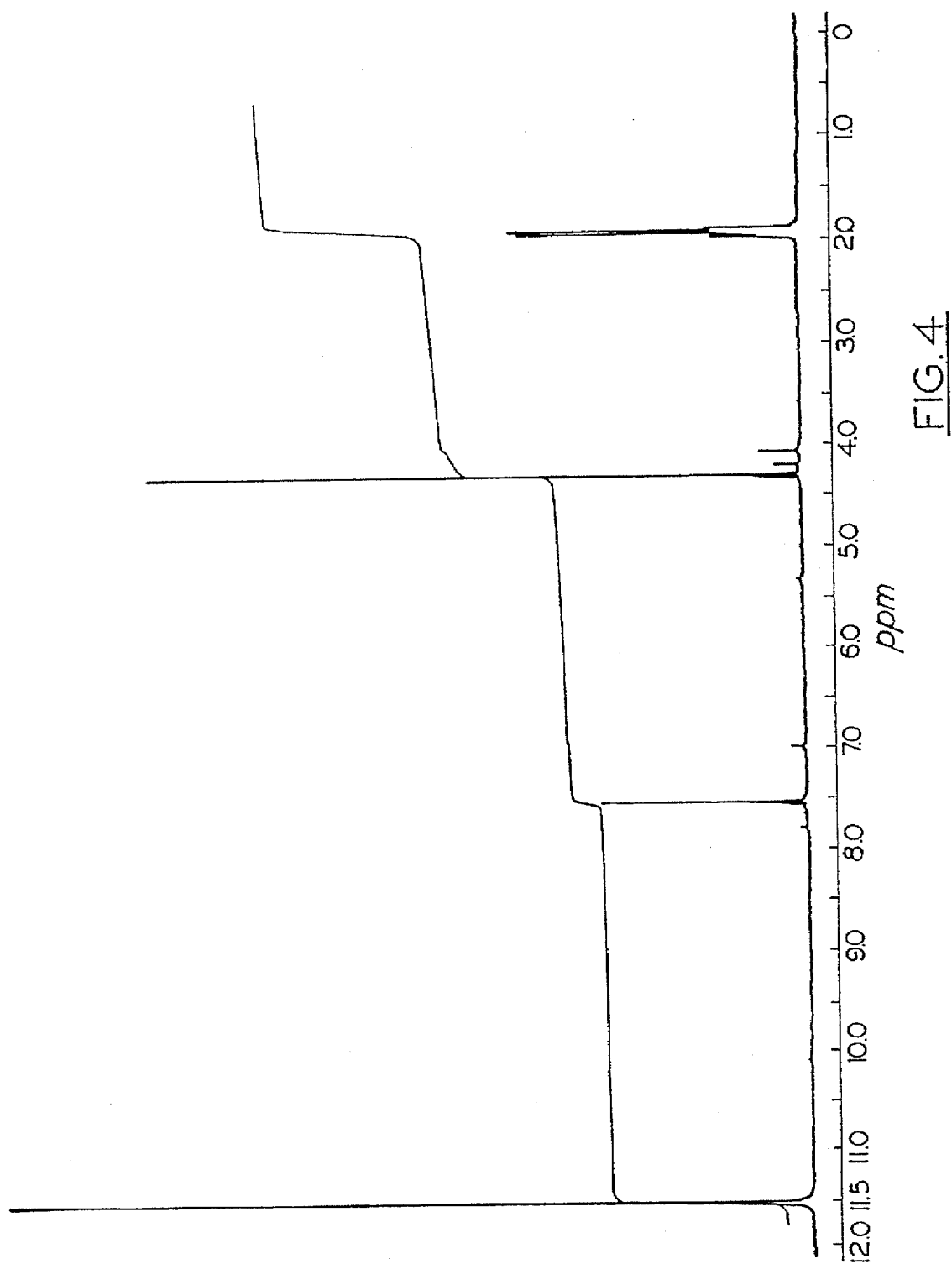
FIG. 4 shows the proton nuclear magnetic resonance spectrum of the product of Example 14 in acetic acid-$d_4$ (100 MHz).

The product of the foregoing experiment was characterized by proton nuclear magnetic resonance spectrum in acetic acid-$d_4$ ($^1$H NMR) as shown in FIG. 4 which shows the H5 at 7.56 ppm and $CH_3$ at 4.31 ppm. The $^1$H NMR spectrum is consistent with a product of the title compound having the anti-isomer configuration and not the syn-isomer as disclosed by said Czechoslovakian patent.

Example 15

Attempted Preparation of 2-(2-Aminothiazol-4-yl)-2-methoxyimino Acetyl Chloride Hydrochloride The general procedure described in Example 7 of U.S. Pat. No. 4,203,899 for the conversion of protected aminothiazolacetic acid to the corresponding acid chloride was applied to the unprotected aminothiazolacetic acid described herein as follows:

A sample of syn 2-(2-aminothiazol-4-yl)-2-methoxyimino acetic acid hydrochloride salt (2.38 g, 0.01 mole) was suspended in 30.5 ml of benzene and cooled to 20° C. Oxalyl chloride (2.09 ml, 0.024 mole) was added, followed by dimethylformamide (0.50 ml, 0.0065 mole). The temperature rose to 22° C. with vigorous gas evolution. Within 20 minutes at 20° C., the gassing had subsided and the slurry was agitated at 20° C.±2° C. for 2 hours. The slurry was concentrated in vacuo to remove the solvent, and the resulting yellow product was dried in vacuo over $P_2O_5$ at 20°–25° C. for 16 hours. Yield was 2.59 g.

The product of the foregoing experiment was characterized by proton nuclear magnetic resonance ($^1$H NMR) spectrum in acetic acid-$d_4$ which shows the H5 at 7.60 ppm and $CH_3$ at 4.37 ppm. The spectrum of the product is consistent with the title compound having the anti-isomer configuration.

Example 16

Attempted Preparation of 2-(2-Aminothiazol-4-yl)-2-methoxyimino Acetyl Chloride Hydrochloride The general procedure described in Example 59 of U.S. Pat. No. 4,203,899 for the conversion of protected aminothiazolacetic acid to the corresponding acid chloride was applied to the unprotected aminothiazolacetic acid described herein as follows:

A sample of syn 2-(2-aminothiazol-4-yl)-2-methoxyimino acetic acid hydrochloride salt (2.38 g, 0.01 mole) was suspended in 25 ml of dichloromethane. After cooling to 4° C., 2.08 g (0.01 mole) of phosphorous pentachloride was added. With ice cooling, the temperature rose to 6° C., and after cooling back to 4° C., the slurry was stirred for 1 hour. The precipitate was collected by filtration under a dry nitrogen atmosphere, washed with dichloromethane (10 ml), and dried in vacuo at 20°–25° C. to give 1.4 g of pale-yellow solid.

The product of the foregoing experiment was characterized by proton nuclear magnetic resonance ($^1$H NMR) spectrum in acetic acid-$d_4$ which shows the H5 at 7.61 ppm and the $CH_3$ at 4.34 ppm. The spectrum of the product is consistent with the title compound having the anti-isomer configuration. Additionally, the product is contaminated with unconverted acid ($^1$H NMR having H5 at 7.07 ppm and $CH_3$ at 4.06 ppm) which was further confirmed by spiking with starting acid.

Example 17

Acylation of 7-Amino-3-[(1-methyl-1-pyrrolidinio) methyl]-ceph-3-em-4-carboxylate HI Salt Using 2-(2-aminothiazol-4-yl)-2-methoxyimino Acetyl Chloride Hydrochloride (Anti-form from Example 14)

To a precooled solution of 9 ml acetone and 3.4 ml water at 10° C. was added 7-amino-3-[(1-methyl-1-pyrrolidinio)methyl]ceph-3-em-4-carboxylate HI salt (1.13 g, 2.66 mmol). 2-(2-Aminothiazol-4-yl)-2-methoxyiminoacetyl chloride hydrochloride (1.09 g, 4.21 mmol) [prepared in Example 14] was added in 5 portions at 0° C. along with triethylamine (0.37 ml, 2.66 mmol) to keep the pH at 6.0–7.0. The reaction mixture was stirred at ambient temperature for 15 minutes. Assay of the resulting solution by high pressure liquid chromatography (gradient $C_{18}$ column, 2% to 25% acetonitrile in 0.005M $NH_4H_2PO_4$) showed 72.4 area percent of anti-cefepime at 13.08 minutes and no detectable syn-cefepime which was expected at about 8.5 minutes retention time. Acidification with sulfuric acid to pH 1.9 gave 1.48 g of anti-cefepime as the sulfate salt. The identification of the product was confirmed by $^1$H NMR spectroscopy (DMSO-$d_6$) and was shown to contain 0.58 mole of triethylamine salt.

Example 18

Acylation of 7-Amino-3-[(1-methyl-1-pyrrolidinio) methyl]ceph-3-em-4-carboxylate HI Salt Using 2-(2-aminothiazol-4-yl)-2-methoxyimino Acetyl Chloride Hydrochloride (Anti-isomer from Example 14)

To a precooled solution of 108 ml of acetone and 40.5 ml of water at 10° C. was added 7-amino-[(1-methyl-1-pyrrolidinio)methyl]ceph-3-em-4-carboxylate HI salt (13.5 g, 0.0317 mol). The pH of the slurry was adjusted to 7.0 using 2.7 ml of 14% $NH_4OH$. With the temperature at 10° C., 2-(2-aminothiazol-4-yl)-2-methoxyimino acetyl chloride hydrochloride (13.05 g, 0.015 mol) [prepared by the procedure of Example 14] was added portionwise over 60 minutes while using 14% $NH_4OH$ (27 ml) to maintain a pH of 6.3–7.0 during the first half of the addition and at pH 6.1–6.6 during the second half of the addition. The reaction mixture was stirred at ambient temperature for 30 minutes. The reaction mixture was polished filtered and washed with 6 ml of 2:1 acetone/water then 6N $H_2SO_4$ (15 ml) was slowly added to the filtrate to adjust the pH to 1.87–1.90. After stirring for 1 hour, the insolubles were filtered off and the cake washed with 21 ml of 2:1 acetone/water and then with 30 ml of acetone. To the filtrate was added 1 liter of acetone over 30 minutes and the mixture was stirred at 5°–8° C. for 40 minutes. The product was collected by filtration, washed twice with 24 ml of 4:1 acetone/water, 60 ml of acetone and dried under vacuum to yield 20.64 g (116% stoich weight) of anti-cefepime as the sulfate salt (95.4% pure by HPLC). The $^1$H NMR spectra was consistent with the structure of anti-cefepime containing about 3 moles of ammonium salts.

Example 19

Comparison of a product of Example 9 (cefepime syn-isomer) and a product of Example 17 (cefepime anti-isomer) show the following differences in physical characteristics.

High pressure liquid chromatography of the cefepime isomers was carried out on a Waters µBondapack $C_{18}$ column (3.9×300 mm) using a solvent system mixture of 1000 ml water containing 2.88 g (0.013 mol) heptane sulfonic acid sodium salt and pH adjusted to 4.0 with acetic acid and 100 ml acetonitrile at a flow rate of 2.0 ml/minute. The products were visualized with a Water Model 450 variable wavelength detector set at 254 λ to give the following results.

|  | Retention Time (min.) |
| --- | --- |
| Syn-isomer of cefepime (Example 9) | 10.5 |
| Anti-isomer of cefepime (Example 17) | 37.8 |

The proton NMR spectra of the syn and anti-methoxime isomers of cefepime as the dihydrochloride salts was carried out on a Bruker AMX-400 FT NMR spectrometer using deuterated dimethyl sulfoxide as the solvent. The reported chemical shifts are referenced to DMSO at 2.49 ppm. The numbering system shown below in the Formula and Table are for convenience only.

Syn- and Anti-cefepime

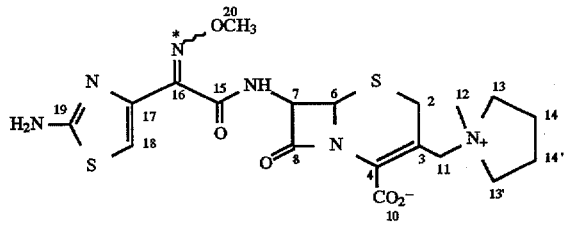

* Wavy bond denotes syn- and anti-methoxyimino isomers.

| Comparison Table of Proton NMR Chemical Shifts (ppm) | | |
| --- | --- | --- |
| Assignment | Syn-Cefepime | Anti-Cefepime |
| C2-H2 | 4.04, 3.65 | 4.02, 3.65 |
| C6-H | 5.33 | 5.31 |
| C7-H | 5.88 | 5.85 |
| C11-H2 | 4.60, 4.31 | 4.59, 4.30 |
| C12-H3 | 2.93 | 2.93 |
| C13-H4 | 3.7, 3.4 | 3.6, 3.3 |
| C14-H4 | 2.10 | 2.10 |
| C18-H4 | 6.88 | 7.57 |
| C20-H3 | 3.92 | 4.05 |
| NH | 9.83 | 9.56 |
| NH2 | 8.60 | 8.70 |

The $^1$H NMR spectra of the two methoxime isomers of cefepime, as shown above, are significantly different. The thiazole ring CH(18) of the syn-(Z) methoxime isomer, at 6.88 ppm, falls upfield of the anti-(E) methoxime isomer CH(18), at 7.57 ppm.

Example 20

Syn 2-(2-Aminothiazol-4-yl)-2-methoxyimino Acetic Acid Hydrochloride Salt

Syn 2-(2-aminothiazol-4-yl)-2-methoxyimino acetic acid (85.3 g, 424 mmol) in dichloromethane (570 mL) was milled under nitrogen for 15 minutes in a blender. The resulting fine suspension was diluted with dichloromethane (100 mL), and transferred under nitrogen to a 1 L Buchi jacketed reactor. The reactor was pressurized with nitrogen (5 psi) and the mixture stirred at 375 rpm and cooled to −2° C. Hydrogen chloride (15.4 g, 424 mmol) was introduced into the headspace of the reactor at 0.2 g per minute. There was a temperature rise of 2° C. The mixture was stirred for a further 30 minutes at 0° C., filtered, and washed with dichloromethane (350 mL) under nitrogen. The solid was dried in vacuo at 45° C. for 18 hours. The title compound was an off-white powder (110.9 g, 111% uncorrected yield).

Anal. Calcd. for $C_6H_8N_3O_3SCl$: C, 30.32; H, 3.39; N, 17.68; S, 13.49; Cl, 14.91; Found: C, 29.37; H, 3.17; N, 16.34; S, 12.70; Cl, 16.99.

$^1$H NMR (DMSO-$d_6$) δ: 4.05 (s, 3H, $CH_3$), 5.9 (s, 15 mole % residual $CH_2Cl_2$), 7.1 (s, 1H, C-5 H). Signals were also seen at 4.18 (s, 3H, $CH_3$) and 7.7 (s, 1H, C-5 H) corresponding to ca. 2% of anti-isomer.

Example 21

Syn 2-(2-Aminothiazol-4-yl)-2-methoxyimino Acetic Acid Hydrochloride Salt

Syn 2-(2-aminothiazol-4-yl)-2-methoxyimino acetic acid (25 g, 124 mmol) in acetonitrile (125 mL) under nitrogen was titrated with a 1.39$\underline{M}$ solution of HCl in acetonitrile (89.2 mL, 123.9 mmol) and was maintained at 10° to 15° C. The mixture was stirred for a further 30 minutes at 10° to 15° C., filtered, and washed with acetonitrile (200 mL) under nitrogen. The solid was dried in vacuo at 45° C. for 3 hours. The title compound was an off-white powder (29.5 g, 97.4% uncorrected yield).

$^1$H NMR (CD$_3$OD) δ: 2.05 (s, 13% wt/wt, residual acetonitrile), 4.1 (s, 3H, $CH_3$), 7.1 (s, 1H, C-5 H). Signals were also seen at 4.2 (s, 3H, $CH_3$) and 7.8 (s, 1H, C-5 H) corresponding to ca. 0.5% of anti-isomer.

Example 22

Syn 2-(2-Aminothiazol-4-yl)-2-methoxyimino Acetyl Chloride Hydrochloride

Syn 2-(2-aminothiazol-4-yl)-2-methoxyimino acetic acid hydrochloride (56.24 g, 210 mmol), containing approximately 11% wt/wt residual acetonitrile) in dichloromethane (450 ml) was milled under nitrogen for 3 minutes in a blender, then cooled to −35° C. and transferred under nitrogen over 5 minutes to a well stirred slurry of Vilsmeier reagent, also at −35° C.

The slurry of Vilsmeier reagent was prepared by adding oxalyl chloride (28.2 g, 221 mmol) portionwise to a solution of dimethylformamide (16.89 g, 231 mmol) in dichloromethane (300 mL) at 0° C., followed by cooling to −35° C. During the addition, the reaction temperature rose to −28° C. After the addition, the reaction mixture was seeded with the product. After a further 2.5 hours at −28° C. to −35° C.

the mixture was filtered and the filter cake washed with dichloromethane (200 mL) under nitrogen. Nitrogen was passed through the cake for 30 minutes, then the solid was dried in vacuo at room temperature for 12 hours. The title compound was obtained as an off-white powder (42.9 g, 72% yield).

$^1$H NMR (CD$_3$OD) δ: 4.06 (s, 3H, CH$_3$), 7.12 (s, 1H, C-5 H). Signals were seen at 7.18 corresponding to ca. 5% of the acid hydrochloride salt, and at 7.80 (s, C-5 H) corresponding to ca. 0.5% of the anti-isomer. After derivatization with diethylamine in acetonitrile, HPLC analysis showed the title compound (syn-isomer, as its diethylamide derivative) with a retention time of 9.6 minutes, the acid hydrochloride salt with a retention time of 2.8 minutes, and the anti-isomer (as its diethylamine derivative) with a retention time of 16.4 minutes. The ratio of the syn-isomer:acid hydrochloride salt:anti-isomer was 90:5:<1.

Example 23

Syn 2-(2-Aminothiazol-4-yl)-2-methoxyimino Acetyl Chloride Hydrochloride

Syn 2-(2-aminothiazol-4-yl)-2-methoxyimino acetic acid (84.7 g, 421 mmol) in dichloromethane (570 mL) was milled under nitrogen for 20 minutes in a blender. The resulting fine suspension was diluted with dichloromethane (100 mL), and transferred under nitrogen to a 1 L Buchi jacketed reactor. The reactor was pressurized with nitrogen (5 psi) and the mixture stirred at 375 rpm and cooled to −2° C. Hydrogen chloride (15.3 g, 421 mmol) was introduced into the headspace of the reactor at 0.2 g per minute. There was a temperature rise of 2° C. The mixture was stirred for a further 30 minutes at 0° C., milled for 3 minutes in the blender, then cooled to −35° C. and transferred under nitrogen over 5 minutes to a well stirred slurry of Vilsmeier reagent, also at −35° C. The slurry of Vilsmeier reagent was prepared by adding oxalyl chloride (56.1 g, 439 mmol) portionwise to a solution of dimethylformamide (33.8 g, 462 mmol) in dichloromethane (880 mL) at 0° C., followed by cooling to −35° C. During the addition, the reaction temperature rose to −28° C. After the addition, the reaction mixture was seeded with product. After a further 2.5 hours at −28° C. to −35° C. the mixture was filtered and the filter cake washed with dichloromethane (350 mL) under nitrogen. Nitrogen was passed through the cake for 30 minutes, then the solid was dried in vacuo at room temperature for 12 hours. The title compound was obtained as an off-white powder (95.2 g, 89% uncorrected yield).

Anal. Calcd. for C$_6$H$_7$N$_3$O$_2$SCl$_2$: C, 28.14; H 2.76; N, 16.41; S, 12.52; Cl, 27.68; Found: C, 28.11; H, 2.62; N, 16.20; S, 12.22; Cl, 26.74.

$^1$H NMR (CD$_3$OD) δ: 4.06 (s, 3H, CH$_3$), 7.12 (s, 1H, C-5 H). Signals were also seen at 7.18 (s, C-5 H) corresponding to ca. 4% of acid hydrochloride salt, and at 7.80 (s, C-5 H) corresponding to ca. 2% of the anti-isomer. After derivatization with diethylamine in acetonitrile, HPLC analysis showed the title compound (as its diethylamide derivative) with a retention time of 9.6 minutes, the starting acid with a retention time of 2.8 minutes, and the anti-isomer (as its diethylamide derivative) with a retention time of 16.4 minutes. The ratio of syn-isomer:starting acid:anti-isomer was 90:4:2.

What is claimed is:

1. A stable, crystalline syn-isomer of 2-(2-aminothiazol-4-yl)-2-methoxyimino acetyl chloride hydrochloride substantially free of the anti-isomer having the formula

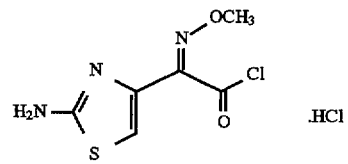

and a proton nuclear magnetic resonance spectrum, as shown in FIG. 1.

2. A process for the preparation of a stable, crystalline syn-isomer of 2-(2-aminothiazol-4-yl)-2-methoxyimino acetyl chloride hydrochloride substantially free of the anti-isomer which comprises reacting the anhydrous crystalline acid hydrochloride salt of the syn-isomer of 2-(2-aminothiazol-4-yl)-2-methoxyimino acetic acid with a mixture containing at least one molar equivalent of oxalyl chloride and at least one molar equivalent to a slight excess of dimethylformamide to an amount of said oxalyl chloride in an inert organic solvent at a temperature of less than −10° C. to produce a stable, crystalline syn-isomer of 2-(2-aminothiazol-4-yl)-2-methoxyimino acetyl chloride hydrochloride substantially free of the anti-isomer.

3. A process of claim 2 further comprising the step of reacting the syn-isomer of 2-(2-aminothiazol-4-yl)-2-methoxyimino acetic acid with at least one molar equivalent of gaseous hydrogen chloride in an inert organic solvent at about 0° C. to room temperature to produce the anhydrous crystalline acid hydrochloride salt of the syn-isomer of 2-(2-aminothiazol-4-yl)-2-methoxyimino acetic acid.

4. A process of claim 3 further comprising isolating said anhydrous crystalline acid hydrochloride salt.

5. A process of claim 2 wherein the amount of oxalyl chloride is 1.0 to about 2.0 molar equivalents and the amount of dimethylformamide is a slight equimolar excess of said oxalyl chloride.

6. A process of claim 5 wherein the amount of oxalyl chloride is 1.05 molar equivalents and the amount of dimethylformamide is 1.075 molar equivalents to said anhydrous crystalline acid hydrochloride salt.

7. A process of claim 2 wherein the solvent is dichloromethane.

8. A process of claim 2 wherein the temperature is about −15° C. to −40° C.

* * * * *